United States Patent [19]

Pawelek et al.

[11] Patent Number: 5,100,654
[45] Date of Patent: Mar. 31, 1992

[54] PHOSPHORYLATED DERIVATIVES OF L-DOPA AND COMPOSITIONS AND METHODS FOR INCREASING THE MELANIN CONTENT IN MAMMALIAN SKIN AND HAIR

[75] Inventors: John M. Pawelek; Michael P. Osber, both of Hamden, Conn.

[73] Assignee: Yale University, New Haven, Conn.

[21] Appl. No.: 334,839

[22] Filed: Apr. 7, 1989

[51] Int. Cl.⁵ .......................... A61K 7/42; C07F 9/06; C07F 9/22; C07F 9/38
[52] U.S. Cl. ...................................... 424/59; 514/114; 514/118; 548/112; 558/178; 560/9; 560/40; 562/9; 562/10; 562/11; 568/442
[58] Field of Search .................... 502/9, 10, 11; 560/9, 560/40; 514/118, 120, 114; 424/59, 60

[56] References Cited

U.S. PATENT DOCUMENTS

| | | | |
|---|---|---|---|
| 4,208,183 | 1/1980 | Grollier et al. | 8/409 |
| 4,508,706 | 4/1985 | Pawelek et al. | 514/107 |
| 4,657,899 | 4/1987 | Rzeszotarski et al. | 562/11 |
| 4,918,064 | 4/1990 | Cordi et al. | 514/114 |

FOREIGN PATENT DOCUMENTS

| | | |
|---|---|---|
| 239826 | 10/1987 | European Pat. Off. . |
| 318935 | 6/1989 | European Pat. Off. ............... 562/11 |
| 2390158 | 5/1977 | France . |
| 2198134 | 6/1988 | United Kingdom . |

OTHER PUBLICATIONS

Körner et al., Science 217, pp. 1163-1165 (1982).
Pawelek et al., Cancer Research 46, 493-497, Feb. 1986.
Pawelek The Journal of Investigative Dermatology, 66: 201-209, 1976.
McLane Biochemical and Biophysical Research Communications, pp. 719-725, vol. 145, No. 2, 1987, Jun. 15, 1987.
Paweler et al., Advances in Pigment Cell Research, pp. 143-154.
Poh Agin et al., Pigment Cell Research 1:137-142, 1987.
Bolognia et al., J. Invest. Dermatology, 1989 (in press).
Bolognia et al., Journal of the American Academy of Dermatology, vol. 19, No. 2, Part 1, p. 217, 1988.
Pawelek Methods for Serum-Free Culture of Neuronal and Lymphoid Cells, pp. 57-66, 1984.

Primary Examiner—Mukund J. Shah
Assistant Examiner—E. Bernhardt
Attorney, Agent, or Firm—Sprung Horn Kramer & Woods

[57] ABSTRACT

A phosphorylated derivative of L-dopa of the formula

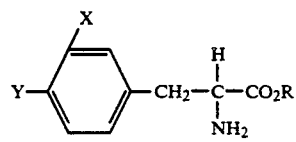

wherein when X is

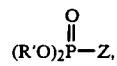

$(R'O)_2\overset{O}{\overset{\|}{P}}-Z$, wherein Z is —CH₂, N, S or a linkage other than oxygen which renders the phosphate group resistant to hydrolysis by phosphatase enzymes in tissues and biological fluids, then Y is OQ, wherein Q is H or an alkyl with one to twelve carbon atoms, or wherein X is OQ, then Y is

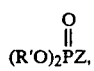

$(R'O)_2\overset{O}{\overset{\|}{P}}Z$, wherein R' is hydrogen or a pharmaceutically acceptable cation and R is a moiety which increases hydropobicity. The phosphorylated derivative of L-dopa is useful as an agent to increase the melanin content in mammalian skin and hair.

17 Claims, 2 Drawing Sheets

PHOSPHORYLATED DERIVATIVES OF L-DOPA AND COMPOSITIONS AND METHODS FOR INCREASING THE MELANIN CONTENT IN MAMMALIAN SKIN AND HAIR

BACKGROUND OF THE INVENTION

1. Field of the Invention

The present invention concerns phosphorylated derivatives of L-dopa and compositions containing the same and methods using such compositions for increasing the melanin content in mammalian skin and hair.

2. Background Information

U.S. Pat. No. 4,508,706 describes the preparation and use of phosphorylated derivatives of L-3,4-dihydroxyphenylalanine ("L-dopa" or "L-DOPA") wherein the phosphoryl groups are esterified via an oxygen linkage to either the 3' or 4' positions of the phenylalanine ring. These isomers are collectively referred to as "dopa phosphates" or "P-DOPA" or "p-dopa".

Using mouse melanoma cells in culture as a model it was found that at relatively high concentrations ($10^{-4}$-$10^{-3}$M) phosphates increase melanin formation and promote cytotoxicity (Pawelek J. and Murray M., *Cancer Research*, 46, 493-497, (1986)). It was shown that these effects were primarily due to the enzymatic removal of the phosphoryl groups and resultant production of L-dopa. It was well-established in many previous studies that L-dopa at high concentrations is cytotoxic to pigment-producing cells and also can be enzymatically converted into melanin by such cells (e.g., Pawelek J., *J. Investigative Dermatology*, 66, 201-209, (1976)).

Also using mouse melanoma cells in culture it was found that low concentrations of dopa phosphates ($10^{-5}$-$10^{-6}$M) were not cytotoxic and by themselves had no noticeable affect on pigment production by the cells. However, at these low concentrations dopa phosphates stimulated a hormone binding system in the cells and increased the cellular responsiveness to the hormone "melanotropin" (also referred to as "melanocyte stimulting hormone" or "MSH") (McLane, J., Osber, M. and Pawelek, J., *Biochem. Biophys. Research Communications*, 145, 719-725, (1987)). An important finding to emerge from the studies on low concentrations of dopa phosphates was that L-dopa itself at such concentrations did not appear to stimulate the MSH binding system in the cells. These observations raised the possibility that the phosphoryl groups must remain esterified to L-dopa in order for there to be a stimulation of the MSH binding system.

Using hairless, pigmented mice and pigmented guinea pigs, it was found that dopa phosphates, but not L-dopa, increased pigmentation in the skin. This effect was best observed when the dopa phosphates were applied in conjunction with low levels of ultraviolet light (Pawelek J., et al, "Advances in Pigment Cell Research" in *Progress in Clinical and Biological Research*, Volume 256, J. E. Bagnara, ed., Alan R. Liss, Inc., N.Y., pp. 143-154, (1988); Agin P. P., Sayre R. M. and Pawelek J., *Pigment Cell Research*, 1, 137-142, (1987)).

Using melanoma cells in culture, mice, and guinea pigs, it was found that ultraviolet light appears to increase melanin content in mammalian skin by stimulating the MSH binding system, much the same as dopa phosphates (Bolognia, J., Murray M. and Pawelek J., *J. Invest. Dermatology*, in pres, (1989)).

EP 238,826 describes a skin-tanning composition containing an indole derivative.

SUMMARY OF THE INVENTION

It is an object of the present invention to provide phosphorylated derivatives of L-dopa.

It is another object of the present invention to provide compositions and methods to increase the melanin content in mammalian skin and hair.

It is a further object of the present invention to increase the effectiveness of dopa phosphates in increasing melanin content in mammalian skin and hair.

It is believed that the phosphoryl group in L-dopa must be intact in order for the dopa phosphates to effectively stiumulate the mammalian pigmentary system. However, biological fluids are rich in phosphatase enzymes which can remove the phosphate groups. A primary feature of this invention is a substitution of oxygen linkage between phosphoryl groups and the phenylalanine ring with atoms that are poorly or not at all recognized by phosphatase enzymes, such as carbon, nitrogen or sulfur atoms. A second feature of this invention is to attach hydrophobic side chains to the substituted dopa phosphates in order to increase hydrophobicity of the molecules—thus increasing the potential for penetration into the dermal layer of mammalian skin.

The above objects and other objects, aims and advantages are satisfied by the present invention which provides a phosphorylated derivative of L-dopa of the formula

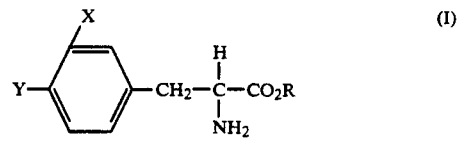

wherein when X is

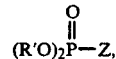

wherein Z is $CH_2$—, N, S or a linkage other than oxygen which renders the phosphate group resistant to hydrolysis by phosphatase enzymes in tissues and biological fluids, then Y is OQ, wherein Q is H or an alkyl with one to twelve carbon atoms, or wherein X is OQ, then Y is

wherein R' is hydrogen or a pharmaceutically acceptable cation and R is a moiety which increases hydrophobicity, e.g., hydrogen, a pharmaceutically acceptable cation, an alkyl having one to twelve carbon atoms, an alkenyl having two to twelve carbon atoms, an alkinyl having two to twelve carbon atoms, an alkoxy having one to twelve carbon atoms, an aryl, a cycloalkyl having three to eight carbon atoms, a heterocyclic having one or more heteroatoms selected from the group consisting of oxygen, sulfur and nitrogen, or a steroid.

The present invention also concerns a composition for increasing the melanin content in mammalian, e.g., human, skin and hair comprising (a) an effective melanin increasing amount of at least one phosphorylated derivative of L-dopa of the formula

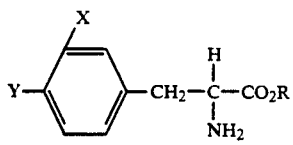
(I)

wherein when X is

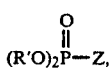

wherein Z is —CH$_2$, N, S or a linkage other than oxygen which renders the phosphate group resistant to hydrolysis by phosphatase enzymes in tissues and biological fluids,
then Y is OQ, wherein Q is H or an alkyl with one to twelve carbon atoms, or wherein X is OQ, then Y is

wherein R' is hydrogen or a pharmaceutically acceptable cation, and R is a moiety which increases hydrophobicity, e.g., hydrogen, a pharmaceutically acceptable cation, an alkyl having one to twelve carbon atoms, an alkenyl having two to twelve carbon atoms, an alkinyl having two to twelve carbon atoms, an alkoxy having one to twelve carbon atoms, an aryl, a cycloalkyl having three to eight carbon atoms, a heterocyclic having one or more heteroatoms selected from the group consisting of oxygen, sulfur and nitrogen, cholesterol and steroids and (b) a pharmaceutically acceptable carrier, e.g., a solid, liquid or liquefied gaseous diluent, or a sterile and/or a physiologically isotonic aqueous solution.

The present invention also relates to a method for increasing the melanin content of mammalian skin and hair comprising administering to a mammal an effective melanin increasing amount of a phosphorylated derivative of L-dopa of the formula

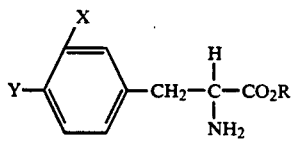
(I)

wherein when X is

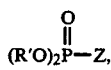

wherein Z is —CH$_2$, N, S or a linkage other than oxygen which renders the phosphate group resistant to hydrolysis by phosphatase enzymes in tissues and biological fluids,
then Y is OQ, wherein Q is H or an alkyl with one to twelve carbon atoms, or
wherein X is OQ, then Y is

wherein R' is hydrogen or a pharmaceutically acceptable cation and R is a moiety which increases hydrophobicity, e.g., hydrogen, a pharmaceutically acceptable salt, alkyl, alkoxy, alkenyl, alkinyl, aryl, cycloalkyl, heterocyclic, cholesterol or a steroid, either alone or in admixture with a pharmaceutically acceptable carrier,

DETAILED DESCRIPTION OF THE INVENTION

Figure 1:
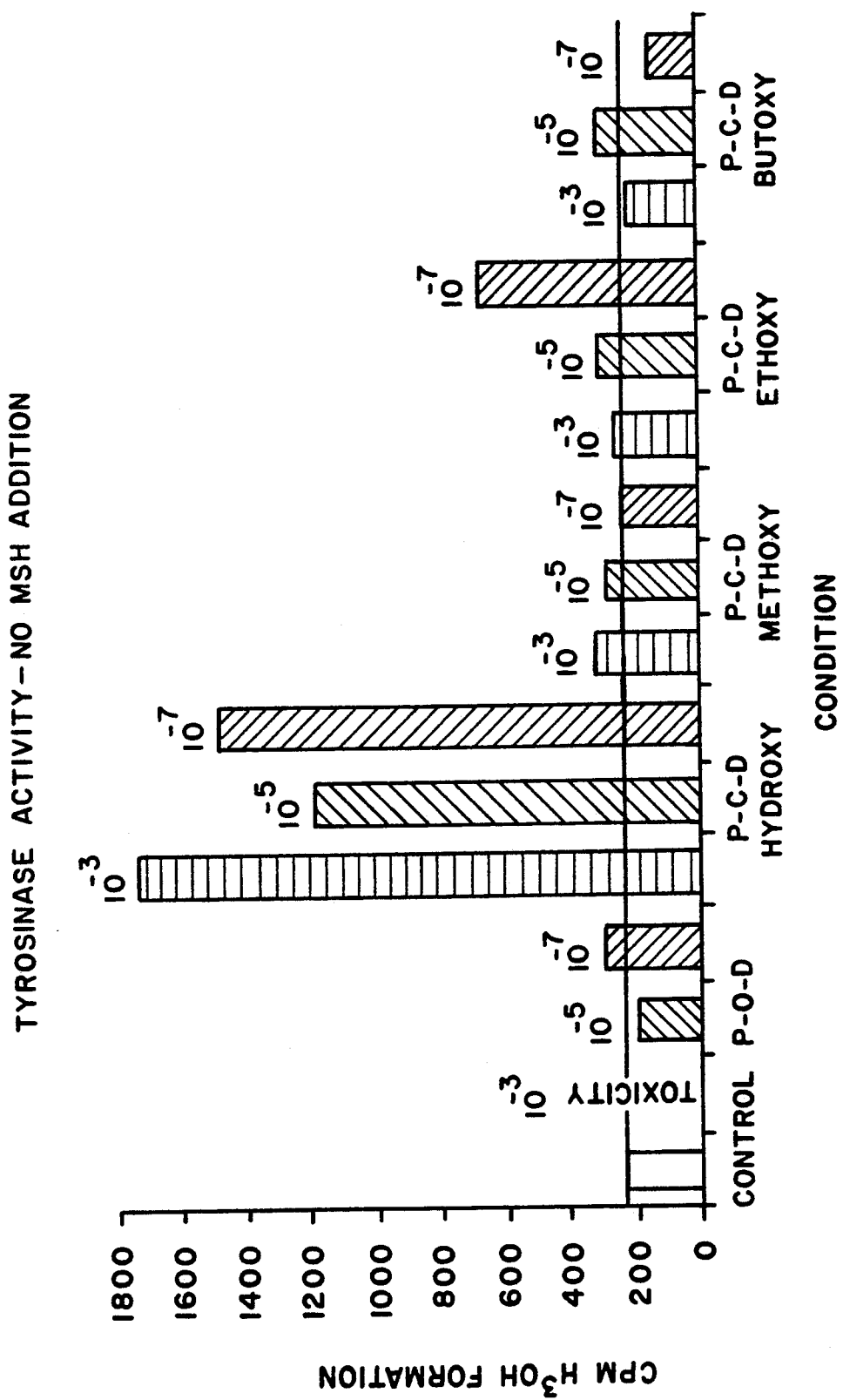
FIG. 1 is a series of bar graphs depicting tyrosinase activity in cultured melanoma cells with no addition of MSH for p-dopa and for compounds according to the invention.

The present invention relates to analogs of phosphorylated L-dopa wherein the phosphate group is attached to the 3' position of the phenylalanine ring via a carbon linkage and to compositions employing the same and methods of increasing the melanin content of mammalian skin and hair using such compositions. Furthermore, the 4' position of the phenylalanine ring is occupied by a hydroxyl group which may be modified (substituted) by the addition of other compounds such as, for example, methyl, ethyl, or butyl side chains, or other such chains which increase hydrophobicity of the molecule.

Still further, the invention concerns analogs of phosphorylated L-dopa wherein the phosphate group is attached to the 3' position of the phenylalanine ring via a nitrogen or sulfur linkage of any such linkage which differs from oxygen and which renders the phosphate group resistant to hydrolysis by phosphatase enzymes in tissues and biological fluids and to compositions containing the same and methods of increasing the melanin content of mammalian skin and hair using such compositions.

In addition, the invention also is directed to analogs of phosphorylated L-dopa wherein the phosphate is attached to the 4' position of the phenylalanine ring via a carbon, nitrogen or sulfur linkage or any linkage which differs from oxygen and which renders the phosphate group resistant to hydrolysis by phosphatase enzymes and to compositions containing the same and methods of increasing the melanin content of mammalian skin and hair using such compositions. In the case where the phosphate is attached to the 4' position of the phenylalanine ring, the 3' position of the phenylalanine ring is occupied by a hydroxyl group which may be modified by the addition of other compounds such as, for example, methyl, ethyl or butyl side chains, or other chains which increase the hydrophobicity of the molecule.

The salt forms which are most useful in accordance with the invention are those where the cations are pharmaceutically acceptable cations selected from the group consisting of metal cations, both mono- and polyvalent, triethanolamine; tris(hydroxymethyl)aminomethane, and similar cations which are not readily oxidized or reduced.

Illustrative of the metal cations which are useful in accordance with the invention are sodium, potassium, calcium and magnesium, and the like. Easily oxidized or reduced cations which may not be used in the practice of the invention include those of iron and copper. Preferred cations for use in accordance with the invention include the non-oxidizable and non-reducible cations such as triethanolamine-tris(hydroxymethyl)aminomethane, sodium and potassium.

Furthermore, in the event that the composition is to be administered orally or parenterally the choice of cation will depend upon the subject's medical history, e.g., if the subject is on a salt-free diet the cation should not be sodium.

In formula (I) alkyl represents a straight-chain or a branched hydrocarbon radical having 1 to 12 carbon atoms. Lower alkyl having 1 to about 6 carbon atoms is preferred. Non-limiting examples of alkyl are methyl, ethyl, propyl, isopropyl, butyl, isobutyl, pentyl, isopentyl, hexyl, isohexyl, heptyl, isoheptyl, octyl and isooctyl.

In formula (I) for R, cycloalkyl represents a cyclic hydrocarbon radical having 3 to 8 carbon atoms. The cyclopentane and the cyclohexane rings are preferred. Non-limiting examples of cycloalkyl are cyclopentyl, cyclohexyl, cycloheptyl and cyclooctyl.

In formula (I) for R, alkoxy represents a straight-chain or branched hydrocarbon radical which has 1 to 12 carbon atoms and is bonded via an oxygen atom. Lower alkoxy having 1 to 6 carbon atoms is preferred. An alkoxy radical having 1 to 4 carbon atoms is particularly preferred. Non-limiting examples of alkoxy are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In formula (I) for R, aryl represents an aromatic radical having 6 to 12 carbon atoms. Preferred aryl radicals are phenyl, naphthyl and biphenyl. Also aryl includes substituted aryl such as phenoxy and phenylthio.

In formula (I) the alkyl, cycloalkyl, alkoxy, aryl, alkinyl, alkenyl and heterocyclic may be unsubstituted or substituted by one or more substitutents such as halogen, e.g., chlorine, fluorine, iodine and bromine, nitro, cyano, hydroxy or amino. Aryl, heteroaryl and cycloalkyl may also be substituted by an alkyl having 1 to 12 carbon atoms.

Non-limiting examples of heterocyclic rings for R in formula (I) include furan, furfural, pyrrole, pyrrolidine, pyrroline, proline, pyrazole, pyridine, thiophene, imidazole, oxazole, thiazole, pyrimidine, purine, quinoline and carbazole.

In formula (I), steroid refers to a family of compounds that contain the perhydro-1,2-cyclopentanophenanthrene ring. Non-limiting examples of steroids include cholesterol, estradiol, progesterone, testosterone and androsterone.

Pharmaceutically acceptable carriers useful in the practice of the invention are known in the art and include, for injection—distilled water; for controlled release—microcapsules comprising carboxymethylene copolymers; for transdermal release-acrylamides and for topical application—cosmetic bases.

In addition, if desired, the composition according to this embodiment comprises at least one additive selected from the group consisting of solvents, fragrances, sunscreening agents, preservatives and chelating agents.

Cosmetic bases useful in the practice of the invention are well known and include lotions, creams, ointments and dusting powders. Examples thereof may be found in, e.g., U.S. Pat. Nos. 4,228,151; 4,282,206 and 2,949,403.

Solvents for use in accordance with the invention include ethanol, isopropyl alcohol, benzyl alcohol, oils, for example, ground nut oil, distilled and/or deionized water, physiological saline solution and the like. The specific solvent chosen will depend on the method of application.

Fragrances useful in the preparation of compositions for tanning or sun-tanning are known, per se, and need not be discussed further.

It may also be desirable to add a preservative to the inventive compositions if they are to be used for topical applications.

Preservatives are well known and may be exemplified by methylparaben, "DOWACIL 2000" and propylparaben.

Sunscreening agents for topical use in accordance with the invention include most commercially available screening agents especially those described by the Monograph On Sunscreens, Fed. Register, Par 2, 43 (Aug. 25, 1978) as safe and effective. Additional sunscreening agents are described in, for example, U.S. Pat. Nos. 4,264,581; 2,949,403 and 4,256,664.

As compositions comprising the inventive phosphorylated L-DOPA derivatives may be deactivated by reducible or oxidizable cations, such as those of copper or iron, or even by excess amounts of multivalent cations, such as calcium or magnesium it is often desirable to have such compositions contain chelating agents, many of which are known in the art, such as ethylenediaminetetraacetic acid (EDTA).

If desired, in order to reduce the acidity or basicity of the compositions, bases, acids or buffers may be added thereto in accordance with the knowledge of the art.

When applied topically to mammalian skin, transdermally or injested orally, the aforesaid compositions increase melanin content of skin and hair. Increases in melanin content are most marked when the inventive compositions are used in conjunction with low levels of ultraviolet light, such uv light or radiation applied during or after administration of the melanization increasing composition. Such levels of ultraviolet light when used by themselves elicit little or no increase in the melanin content of skin.

In accordance with another embodiment of the invention there is also provided a method of imparting a "tan" coloration to a subject, even one having a low concentration of epidermal melanocytes, for instance subjects suffering from vitiligo or other disorders of hypopigmentation, for example, oculocutaneous albinism, nevus depigmentosus, hypomelanosis of Ito, idiopathic guttate hypomelanosis and pityriasis alba. An excellent review of hypopigmentation is found in Jean L. Bolognia and John M. Pawelek, *Journal of the American Dermatology*, Vol. 19, No. 2, Part 1, August 1988, 217-258.

The phosphorylated L-DOPA derivatives according to the present invention are usually present in the melanization increasing compositions in concentrations, based on the total composition, of about 0.005 to about 1.0% wt. A preferred concentration of phosphorylated L-DOPA derivatives according to the present invention is about 0.02% wt.

The compounds of the present invention contain phosphates groups which cannot be cleared enzymatically. This means that the inventive p-dopa is a biologically active compound and not merely a "store-house" for dopa which is produced by enzymatic clevage. It also means that since the phosphate is not cleaved, there is no limit to the concentration that can be used since the material cannot act as a depigmenting agent because free dopa and free radicals are not produced.

The present invention will now be described with reference to the following non-limiting examples.

EXAMPLES

The following examples describe the synthesis of dopa phosphates wherein the phosphoryl groups are attached to the phenylalanine ring at the 3' position through a carbon atom linkage (referred to as 3' phosphoryl-carbonyl dopa phosphates, or "3-P-C-D"). Four subsets of these molecules have been synthesized and tested for their ability to stimulate the pigmentary system, namely, the following
3-P-C-D with a 4' hydroxyl group;
3'-P-C-D with a 4' methoxy group;
3'-P-C-D with a 4' ethoxy group;
3'-P-C-D with a 4' butoxy group.

Each of the above compounds is effective in stimulating the pigmentary system of melanoma cells in culture. The compounds are not cytotoxic at high concentrations indicating the L-dopa cannot be produced through cleavage of the phosphoryl bonds by cellular phosphatase enzymes. Each of these compounds exhibits stimulation of the pigmentary systems of guinea pigs when applied in conjuction with low levels of ultraviolet light. The ethoxy- and butoxy-derivatized compounds are most effective in culture and on guinea pigs. The following conclusions can be stated from these test on biological activity:

(a) an intact phosphoryl group is necessary for stimulation of the pigmentary system;
(b) the addition of longer hydrophobic side chains (e.g., pentoxy-, octoxy-, dodecoxy-) or different types of hydrophobic side chains (e.g. steroids, cholesterol) may increase the potency of the P-C-D toward the pigmentary system;
(c) 4'-P-C-D with hydrophobic substitutions at the 3' position may also be potent stimulators of the pigmentary system;
(d) substitution of oxygen linkages with atoms other than carbon atoms may also yield active molecules.

Non-limiting examples of commercially available benzaldehydes as starting materials for the compounds of the invention include the following: hydroxy, methoxy, ethoxy, propoxy, 2-propoxy, butoxy, pentyloxy, amyloxy, hexyloxy, heptyloxy, octyloxy, nonyloxy, decyloxy, and dodecyloxy.

EXAMPLE 1

4-Hydroxy-3-Chloromethylbenzaldehyde (1)

Through a well-stirred suspension of 0.1 mole 4-hydroxybenzaldehyde, 88ml concentrated HCl and 8.8ml 37% aqueous formaldehyde was bubbled HCl gas for approximately 4 hours. A product had fallen out of solution. The reaction mixture was refrigerated for 1.5 hours and then the product was isolated on a scintered-glass funnel and washed with a total of 1 liter cold water. mp 123°–124° C.

EXAMPLE 2

2-Hydroxy-5-Formylbenzylphosphonic Acid Diethyl Ester (2)

0.1 mole 4-Hydroxy-3-chloromethylbenzaldehyde was stirred in 75ml acetonitrile and 0.1 mole triethyl phosphite was added dropwise into the stirring suspension. After all the triethyl phosphite had been added, the reaction was refluxed for 4 hours. The reaction was then cooled to room temperature. The reaction solution was then filtered and the acetonitrile was removed on a rotary evaporator leaving behind a solid. This was recrystallized from THF:hexanes in a −20° C. freezer. The product was isolated on a buchner funnel and washed with −20° C. THF. mp 88°–88.5° C.

EXAMPLE 3

2-Hydroxy-5-Formylbenzylphosphonic Acid (3)

0.1 mole 2-Hydroxy-5-formylbenzylphosphonic acid diethyl ester was refluxed for 3 hours with 100 ml 6N HCl. Product was separated out while it was being formed. The reaction solution was cooled in the refrigerator and the product was isolated on a buchner funnel and washed with cold water. mp 252°–253° C.

EXAMPLE 4

5-[4-Hydroxy-3-Phosphonomethyl]benzylidenehydantoin (4)

0.1 mole 2-Hydroxy-5-formylbenzylphosphonic acid, 0.1 mole hydantoin, 0.05 mole glycine and 100 ml water were stirred together. The pH of the solution was adjusted to approximately 9.5 with 12.5N NaOH. The reaction was then heated to approximately 85° C. for 3 hours. The reaction solution was then filtered and the filtrate was adjusted to pH 1.0 with concentrated HCl. A precipitate formed. The suspension was placed in the refrigerator overnight and the product was isolated on a scintered-glass funnel and washed with cold water. mp 298°–299° C. (dec).

EXAMPLE 5

5[4-Hydroxy-3-Phosphonomethyl]benzyl hydantoin (5)

0.1 mole 5-[4-Hydroxy-3-phosphonomethyl]benzylidene hydantoin, 165 ml water, 18.2g 50% NaOH and 3.0g 5% Pd/C were shaken in a hydrogenator at 50 psig until no more hydrogen was taken up. The reaction mixture was then filtered through a Celite pad and the pad was washed with water. The pH of the filtrate was adjusted to pH 1 with concentrated HCl and the water was removed on a rotary evaporator. The residue was recrystallized from boiling water. mp 201°–203° C.

EXAMPLE 6

4-Hyroxy-3-Phosphonomethyl phenylalanine (6)

0.1 mole 5-[-4-Hydroxy-3-phosphonomethyl]benzyl hydantoin, 0.5 mole LiOH·H$_2$O and 250 ml water were refluxed for 48 hours. The reaction was filtered hot and allowed to cool. The pH of the filtrate was then adjusted to 1 with concentrated HCl. The water was then removed on a rotary evaporator. The residue was recrystallized from boiling water with activated charcoal added.

The reaction scheme for the above compounds (1) to (6) is as follows:

Synthesis of Hydroxy Analog

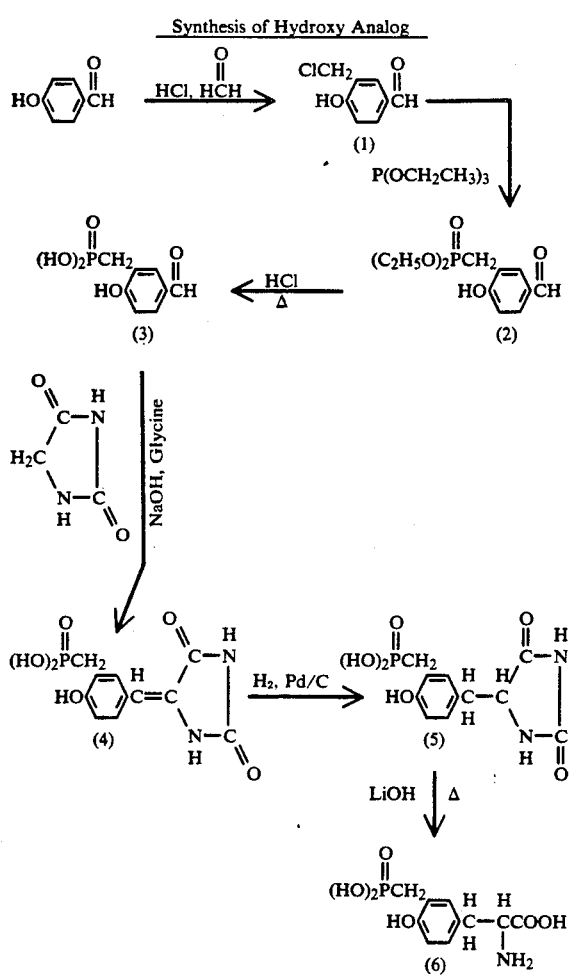

EXAMPLE 7

4-Methoxy-3-Chloromethylbenzaldehyde (1a)

0.1 mole of 4-Methoxybenzaldehyde, 5g ZnCl₂, and 10 ml 37% aqueous formaldehyde were stirred together. Dry HCl gas was then bubbled through the reaction solution for 3 hours. The reaction solution was washed with hot water. The organic phase was taken up by ethanol and the ethanol was removed on a rotary evaporator. The product was crystallized from boiling ethanol. mp 55°–57° C.

EXAMPLE 8

2-Methoxy-5-Formylbenzylphosphonic Acid Diethyl Ester (2a)

In a ratio of 1:1 4-methoxy-3-chloromethylbenzaldehyde and triethyl phosphite were heated together until no more gas evolved. The reaction solution was then vacuum distilled to give the desired product. bp 172°–174° C. at 1 mm Hg.

EXAMPLE 9

5-[4-Methoxy-3-Diethylphosphonomethyl]benzylidene Hydantoin (3a)

0.1 mole 2-Methoxy-5-formylbenzylphosphonic acid diethyl ester, 0.11 mole hydantoin, 0.0225 mole beta-alanine and 40 ml acetic acid were refluxed together for approximately 7 hours and then stirred overnight at room temperature. The reaction was diluted to 330 ml with water and the product isolated on a buchner funnel and washed with water. mp 206°–207° C.

EXAMPLE 10

5-[4-Methoxy-3-diethylphosphonomethyl]benzyl Hydantoin (4a)

0.1 mole 5-[4-Methoxy-3-diethylphophonomethyl]-benzylidene hydantoin, 100 ml water, 8.0g 50% NaOH and 3.0g 5% Pd/C were shaken in a hydrogenator at 50 psig until no more hydrogen was taken up (approximately 3.5 hours). The reaction mixture is filtered through a Celite pad and the pad washed with water. The pH of the filtrate was adjusted to 1 with concentrated HCl. The filtrate was then saturated with NaCl and allowed to stand overnight. The aqueous mixture was extracted with a total of approximately 2 liters of ethyl acetate. The ethyl acetate was dried over anhydrous MgSO₄, filtered, and the ethyl acetate was removed on a rotary evaporator. mp 121√-123° C.

EXAMPLE 11

5-[4-Methoxy-3-Phosphonmethyl]benzyl hydantoin (5a)

To 0.1 mole 5-[4-methoxy-3-diethylphosphonomethyl]benzyl hydantoin were added 250 ml dry chloroform and 0.45 mole bromotrimethylsilane. The reaction was stirred for 2 hours at room temperature. The solvent and excess bromotrimethylsilane were removed on a rotary evaporator and the residue was stirred with 400 ml 95% ethanol for 1 hour. A precipitate formed and was isolated on a scintered-glass funnel and washed once with ethanol/ether and twice with ether. mp 255°–256° C.

EXAMPLE 12

4-Methoxy-3-Phosphonomethyl phenylalanine (6a)

0.1 mole 5-[4-Methoxy-3-phosphonomethyl]benzyl hydantoin, 0.4 mole LiOH·H₂O, and 285 ml water were refluxed together for 24 hours. The reaction solution was filtered hot and allowed to cool. The pH of the solution was then adjusted to approximately 1.9 with concentrated HCl. The water was removed on a rotary evaporator. The product was then recrystallized from boiling methanol. mp 137° C.(dec).

EXAMPLE 13

4-Ethoxy-3-Chloromethylbenzaldehyde (1b)

0.1 mole 4-Ethoxybenzaldehyde, 5g ZnCl₂, and 10 ml 37% aqueous formaldehyde were stirred together. Dry HCl gas was bubbled through the reaction mixture for 4 hours. Ethyl acetate was then added to the reaction mixture and the organic phase was washed with water. The organic phase was dried over anhydrous MgSO₄, filtered, and the ethyl acetate was removed on a rotary evaporator. The residue was recrystallized from boiling methanol. mp 74.5°–75.5° C.

EXAMPLE 14

2-Ethoxy-5-Formylbenzylphosphonic Acid Diethyl Ester (2b)

4-Ethoxy-3-chloromethylbenzaldehyde and triethyl phosphite were added together in a 1:1 ratio and heated until no more gas evolved. The reaction solution was then vacuum distilled to give the desired product. bp 170°–171° C. at 0.75mm Hg.

EXAMPLE 15

5-[4-Ethoxy-3-diethylphosphonmethyl]-benzylidene Hydantoin (3b)

0.1 mole 2-Ethoxy-5-formylbenzylphosphonic acid diethyl ester, 0.11 mole hydantoin, 0.023 moles beta-alanine and 40ml acetic acid were refluxed together for 7 hours. The reaction mixture was then diluted to approximately 400 ml with water. The product was isolated on a buchner funnel and washed thoroughly with water. mp 220°–221° C.

EXAMPLE 16

5-[4-Ethoxy-3-diethylphosphonomethyl]-benzyl Hydantoin (4b)

0.1 mole 5-[4-Ethoxy-3-diethylphosphonomethyl]-benzylidene hydantoin, 135ml water, 10.84 g 50% NaOH and 3.00 g 5% Pd/C were shaken together on a hydrogenator at 50 psig until no more $H_2$ was taken up. The reaction mixture was filtered through a Celite pad and the pad washed with water. The filtrate was adjusted to pH 1 with concentrated HCl. This solution was then saturated with NaCl and allowed to stand overnight. The product was then taken up with ethyl acetate. The ethyl acetate was dried over anhydrous $MgSO_4$, filtered, and the ethyl acetate was removed on a rotary evaporator.

EXAMPLE 17

5-[4-Ethoxy-3-phosphonomethyl]-benzyl Hydantoin (5b)

To 0.1 mole 5-[4-ethoxy-3-diethylphosphonomethyl]-benzyl hydantoin were added to 250ml dry chloroform and 0.45 moles bromotrimethylsilane. The reaction was stirred at room temperature for 3 hours. The solvent and excess bromotrimethylsilane were removed on a rotary evaporator. The residue was stirred with approximately 400 ml 95% ethanol for 1.5 hours. A precipitate formed and was isolated on a scintered-glass funnel and washed with water. mp 242°–244° C.

EXAMPLE 18

4-Ethoxy-3-Phosphonomethyl phenylalanine (6b)

0.1 mole 5-[4-Ethoxy-3-phosphonomethyl]-benzyl hydantoin, 0.4 mole $LiOH \cdot H_2O$ and 300ml water were refluxed together for 24 hours. The reaction solution was filtered hot. The filtrate was cooled and the pH was adjusted to approximately 2 with concentrated HCl. The water was removed on a rotary evaporator and the residue was recrystallized from 150ml boiling water.

EXAMPLE 19

4-Butoxy-3-Chloromethylbenzaldehyde (1c)

0.1 mole 4-Butoxybenzaldehyde, 5g $ZnCl_2$, and 10 ml 37% aqueous formaldehyde were stirred together. HCl gas was bubbled through the reaction solution for approximately 6 hours. The reaction mixture was then stoppered and stirred at room temperature for 48–90 hours. Then ethyl acetate was added to the reaction mixture and the organic phase was washed with water. The organic phase was then dried over anhydrous $MgSO_4$, filtered and the ethyl acetate was removed on a rotary evaporator. The residue was then vacuum distilled to vive the desired product. bp 140° C. at 1.25mm Hg.

EXAMPLE 20

2-Butoxy-5-Formylbenzylphosphonic Acid Diethyl Ester (2c)

4-Butoxy-3-chloromethylbenzaldehyde and triethyl phosphite in a 1:1 ratio were heated until no more gas evolved and the reaction mixture had turned light orange. The reaction mixture was then vacuum distilled to give the desired product. bp 188° C. at 1.4 mm Hg.

EXAMPLE 21

5-[4-Butoxy-3-diethylphosphonomethyl]benzylidenehydantoin (3c)

0.1 mole 2-Butoxy-5-formylbenzylphosphonic acid diethyl ester, 0.11 mole hydantoin, 0.0225 mole beta-alanine and 40 ml acetic acid were refluxed together for approximately 6.5 hours. The reaction mixture was then stirred at room temperature overnight. A solid which formed was diluted to 500 ml with water and the solid was broken into small pieces. The product was isolated on a buchner funnel and washed with water. mp 197.5°–200.5° C. 1.0g of product was recrystallized from a boiling solution of 10 ml water and 11 ml DMSO. mp 206.5°–207° C.

EXAMPLE 22

5-[4-Butoxy-3-diethylphosphonomethyl]benzyl Hydantoin (4c)

0.1 mole 5-[4-Butoxy-diethylphosphonomethyl]-benzylidene hydantoin, 115ml water, 9.61 g 50% NaOH, 16 ml ethanol and 3.07 g 5% Pd/C were shaken together on a hydrogenator at 50 psig until no more hydrogen was taken up (approximately 3 hours). The reaction mixture was filtered through a Celite pad and the pad washed with 12.5% ethanol. The pH of the filtrate was adjusted to 1 with concentrated HCl and the filtrate was saturated with NaCl and allowed to stand overnight. The reaction mixture was extracted with a total of approximately 750ml ethyl acetate. The ethyl acetate was dried over anhydrous MgSO, filtered and the ethyl acetate was removed on a rotary evaporator. The residue was dissolved in 200ml boiling ethyl acetate and cooled to 0° C. overnight. The product was isolated on a scintered-glass funnel and washed with 0° C. ethyl acetate. mp 133°–134° C.

EXAMPLE 23

5- 4-Butoxy-3-Phosphonomethyl benzyl hydantoin (5c)

To 0.1 mole 5-[4-butoxy-3-diethylphosphonomethyl]-benzyl hadantoin were added 25 ml dry chloroform and 0.45 mole bromotrimethylsilane. The reaction was stirred at room temperature for 3 hours. The solvent and the excess bromotrimethylsilane were removed on a rotary evaporator. The residue was stirred for 1 hour with 800 ml 95% ethanol. A precipitate formed and was isolated on a scintered-glass funnel and washed with ether. mp 252°–253° C.

EXAMPLE 24

4-Butoxy-3-Phosphonomethyl phenylalanine (6c)

0.1 mole 5-[4-Butoxy-3-Phosphonomethyl]benzyl hydantoin, .4 mole $LiOH \cdot H_2O$ and 25ml water were refluxed together for 24 hours. The reaction was filtered hot. The filtrate was allowed to cool and the pH was adjusted to approximately 2 with concentrated HCl. An oily precipitate resulted which was recerystallized from boiling water-ethanol.
A reaction scheme encompassing Examples 7 to 24 is as follows:
EXAMPLE 25
Attaching the P-C Group to the 4' Position of the Phenylalanine Ring
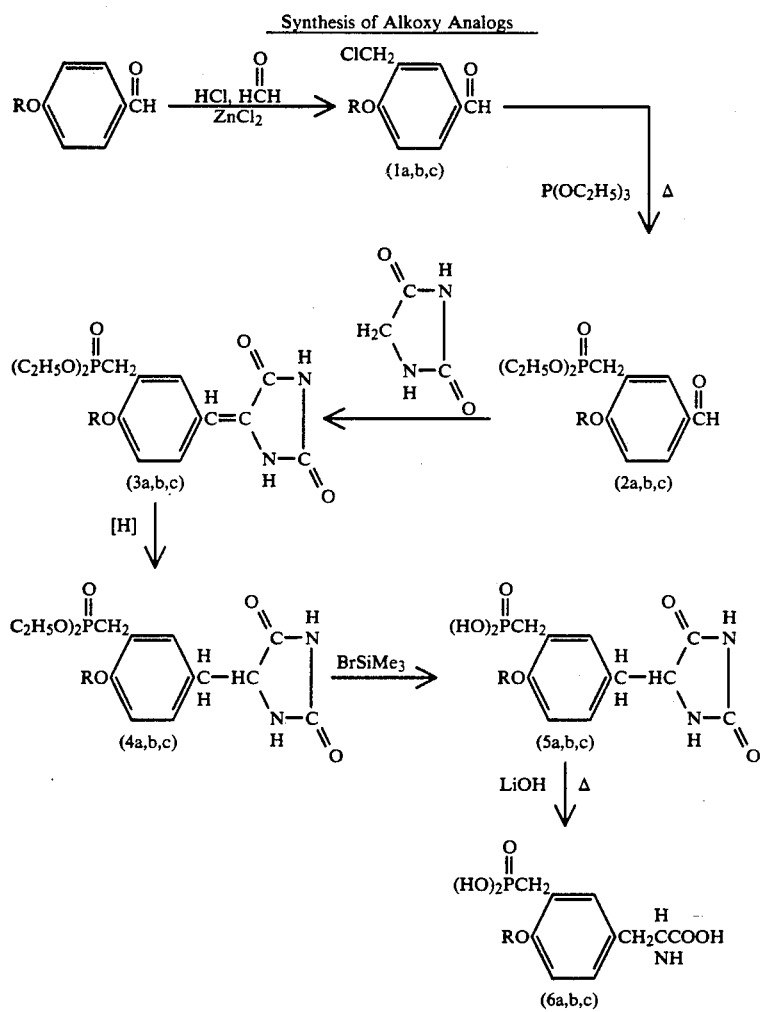
a, R = CH$_3$
b, R = CH$_3$CH$_2$
c, R = CH$_3$CH$_2$CH$_2$CH$_2$
In the following reaction schemes, all temperatures are in degrees centrigrade.
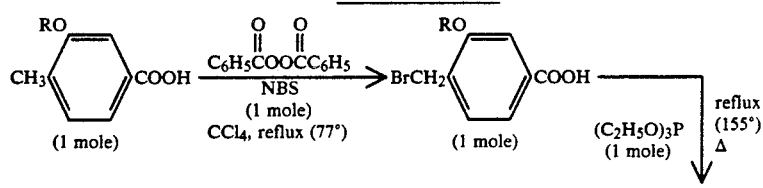

Reaction Scheme I
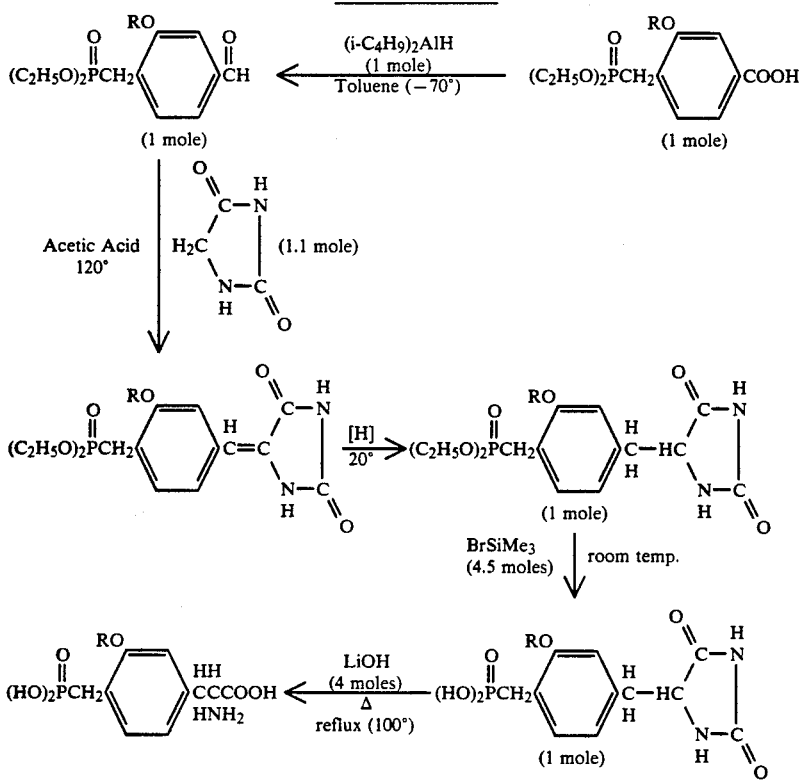
R = H, CH$_3$
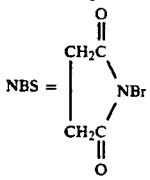
Reaction Scheme II
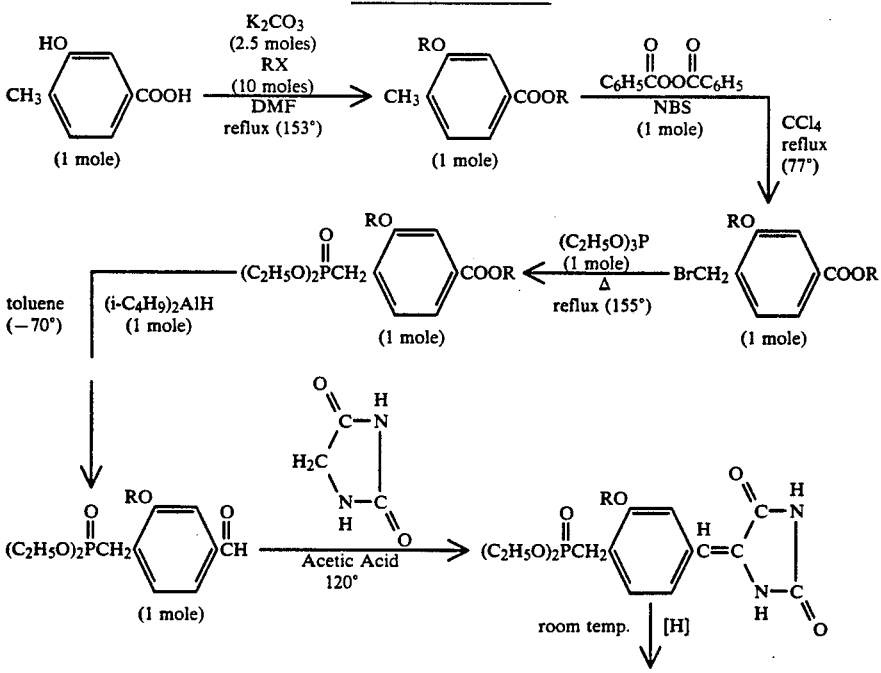

-continued
Reaction Scheme II
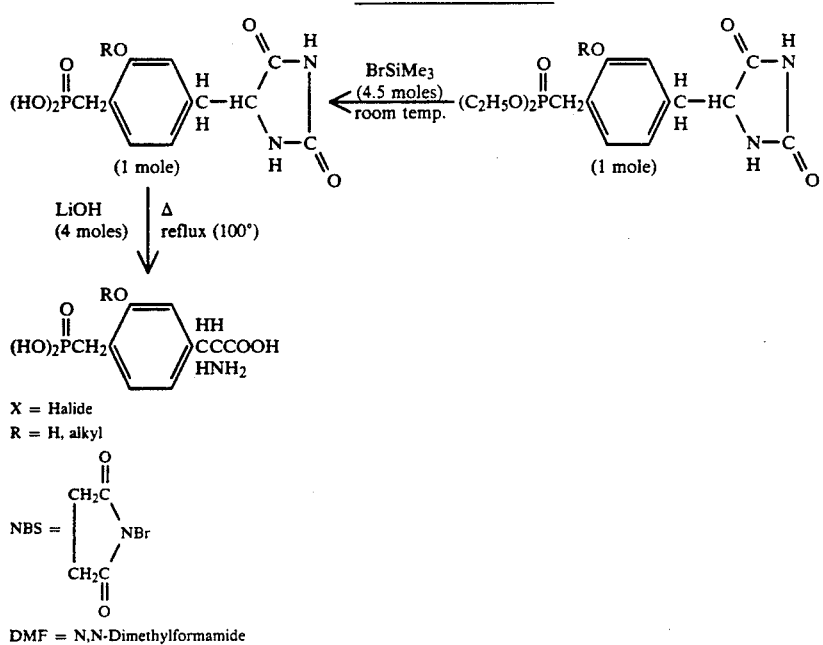
X = Halide
R = H, alkyl
NBS = (structure shown)
DMF = N,N-Dimethylformamide
EXAMPLE 26
Nitrogen Derivatives of Phosphorylated Derivatives of L-Dopa
In the following reaction schemes all temperatures are in degrees centigrade.
Reaction Scheme III
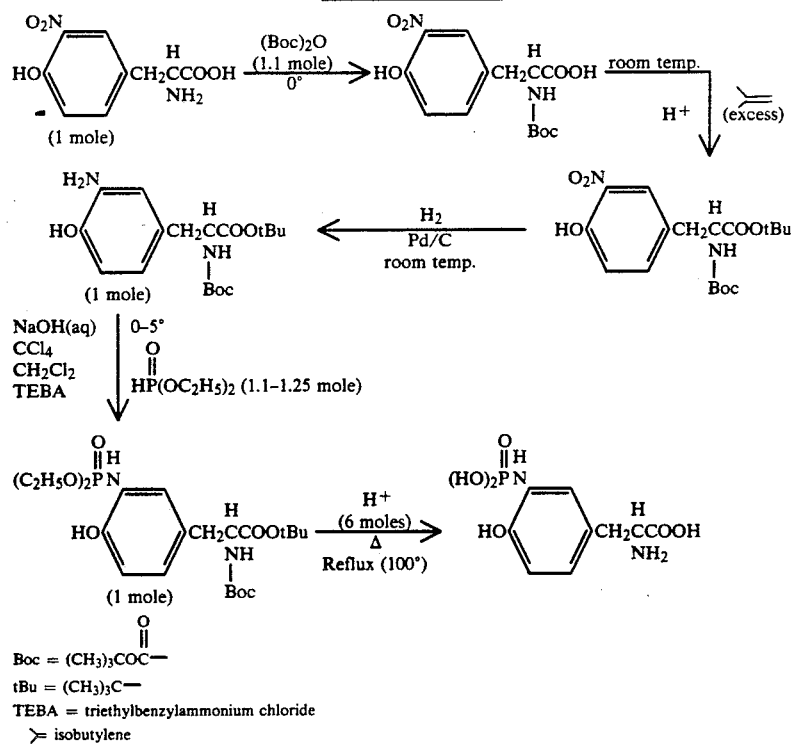
Boc = $(CH_3)_3COC-$
tBu = $(CH_3)_3C-$
TEBA = triethylbenzylammonium chloride
⟩= isobutylene Reaction Scheme IV
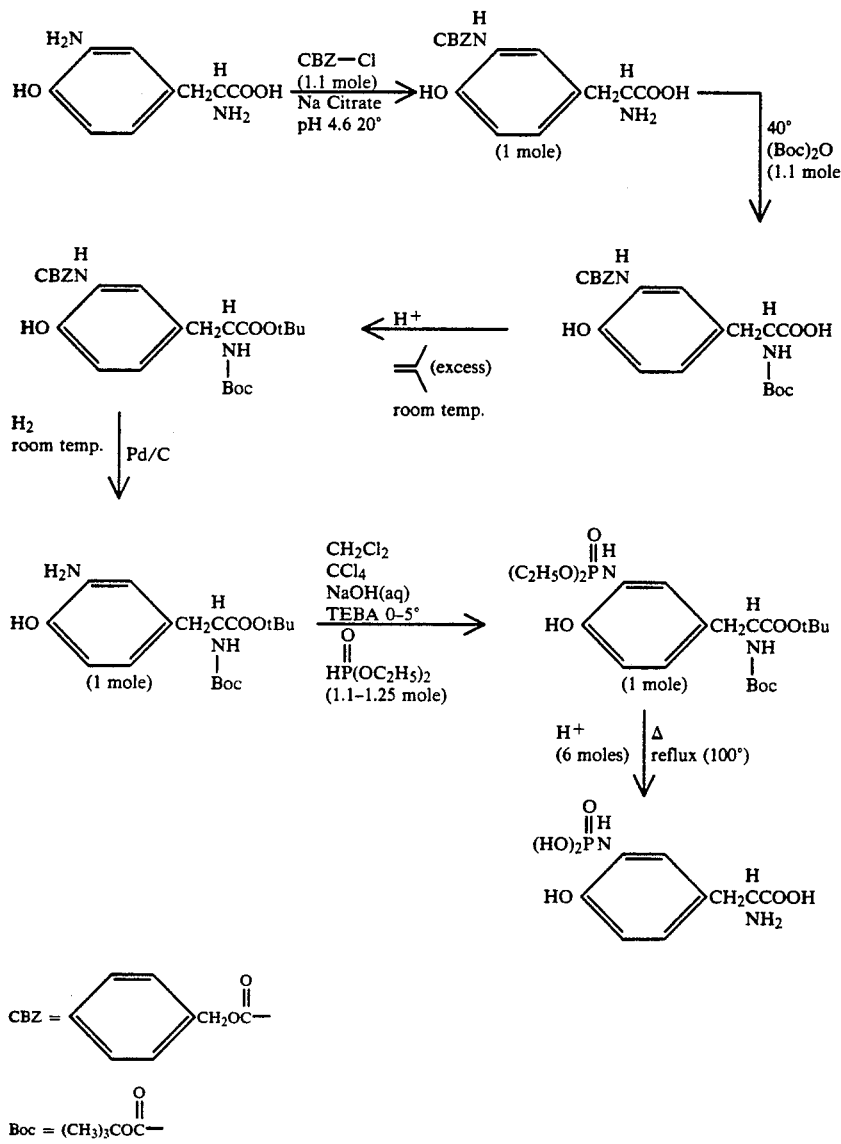
CBZ = <benzyl-OC(O)->
Boc = (CH₃)₃COC(O)-
⧹=⧸ = isobutylene
TEBA = triethylbenzylammonium chloride
Reaction Scheme V
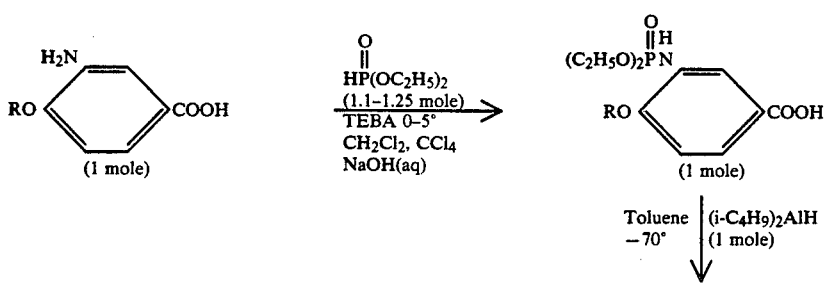

Reaction Scheme V
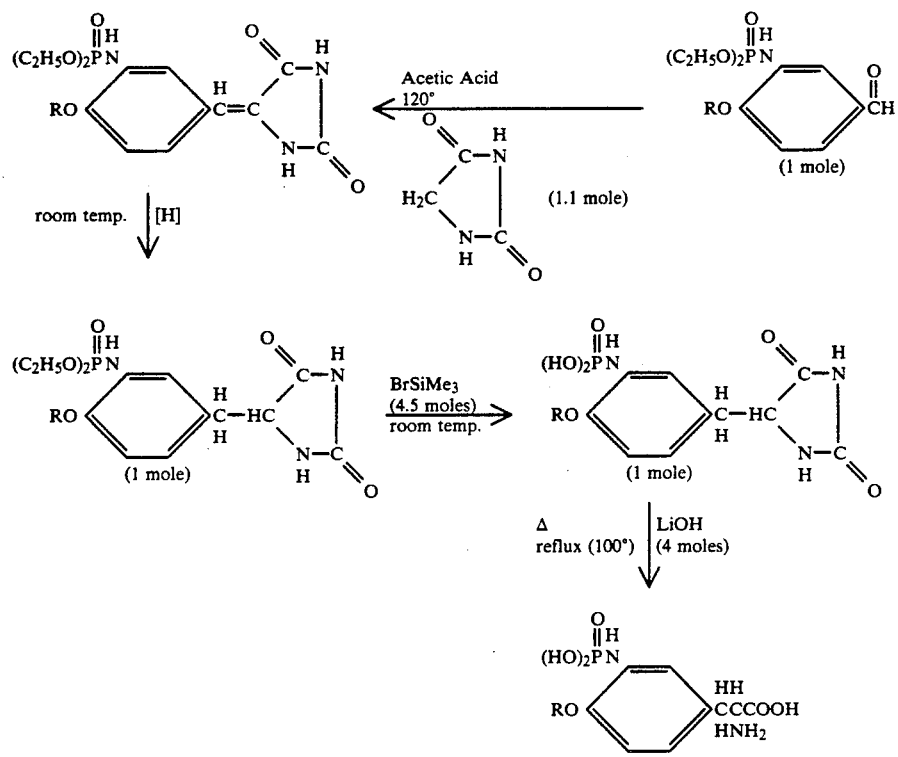
R = H, CH₃
TEBA = triethylbenzylammonium chloride
Reaction Scheme VI
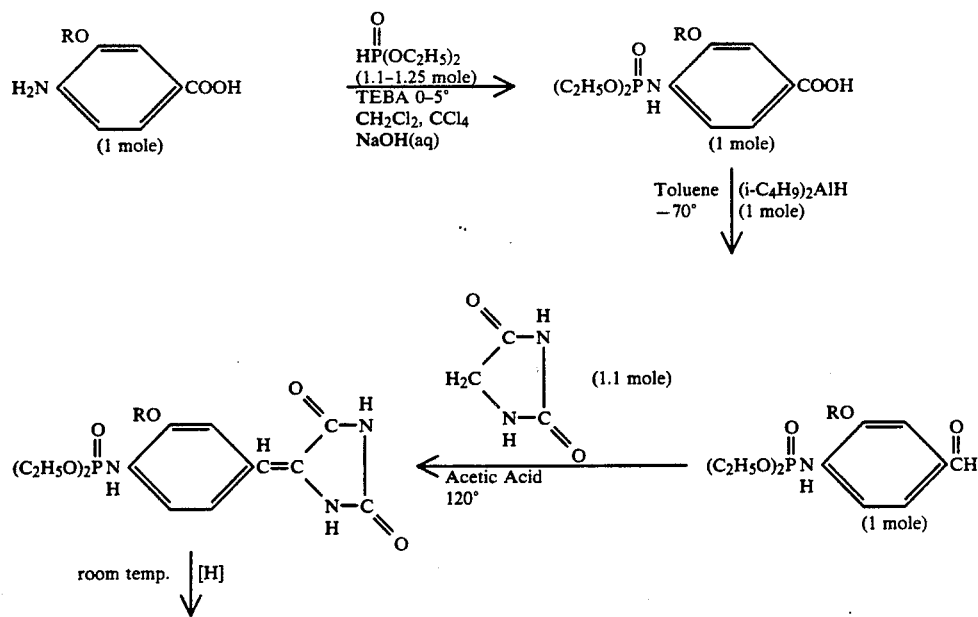

-continued
Reaction Scheme VI
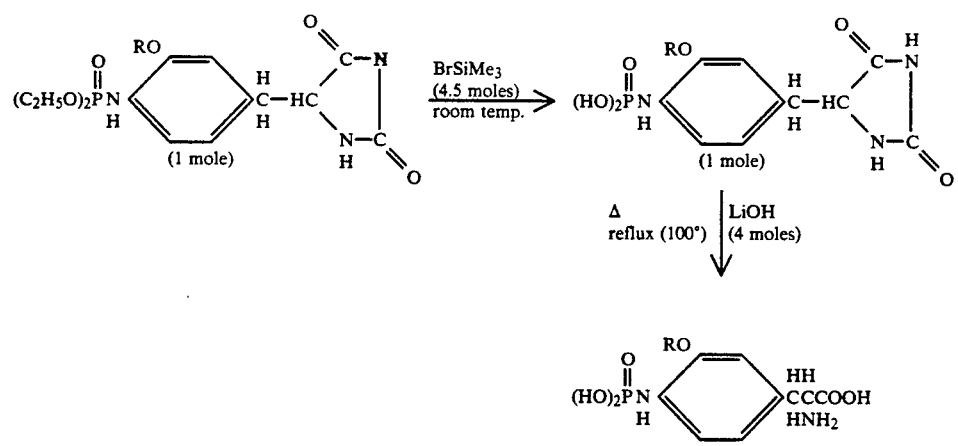
R = H, CH₃
TEBA = triethylbenzylammonium chloride
Reaction Scheme VII
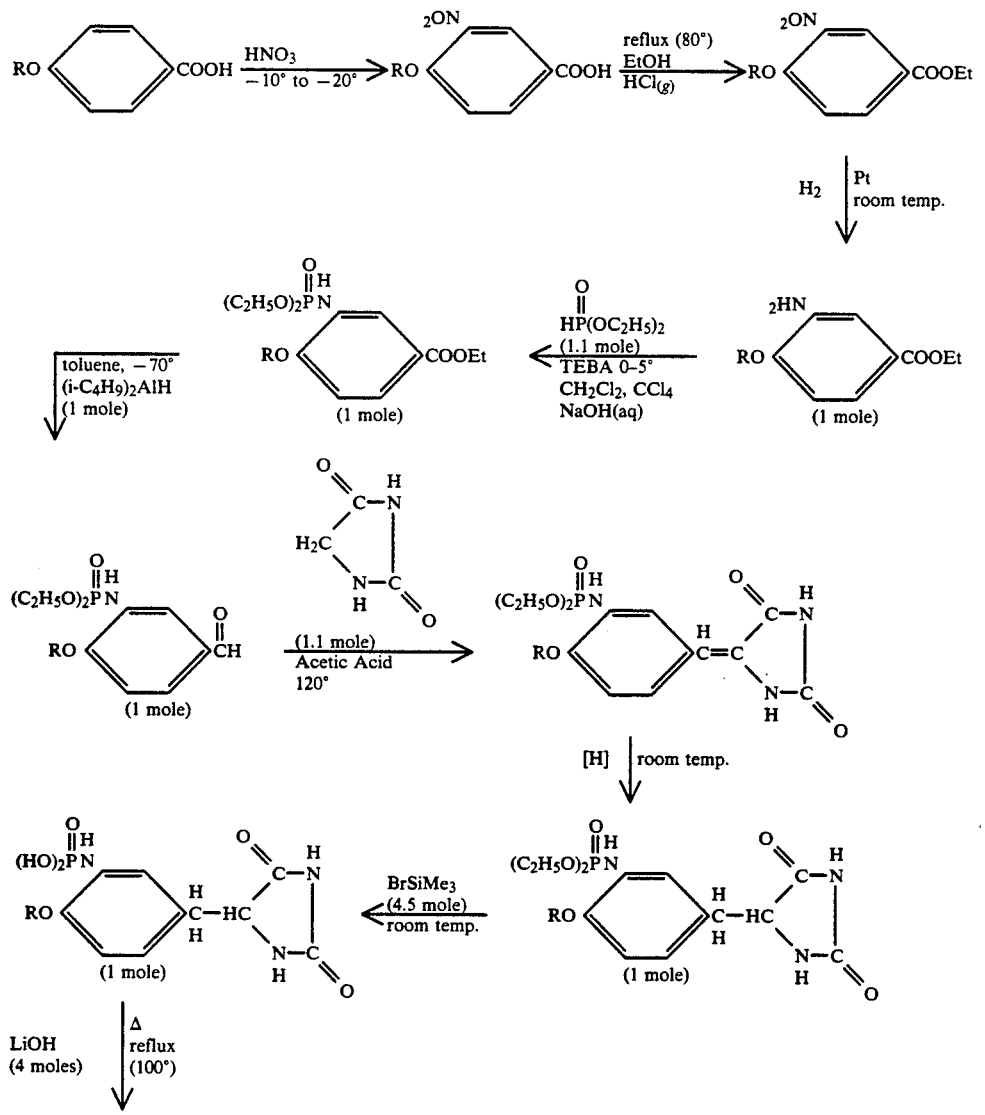

-continued
Reaction Scheme VII

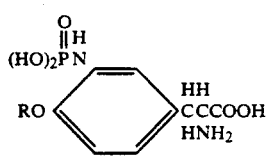

R = H, methyl, ethyl, propyl, butyl, amyl, pentyl, hexyl, heptyl, octyl, nonyl, decyl, undecyl, dodecyl, and hexadodecyl
Et = $CH_3CH_2$
TEBA = triethylbenzylammonium chloride

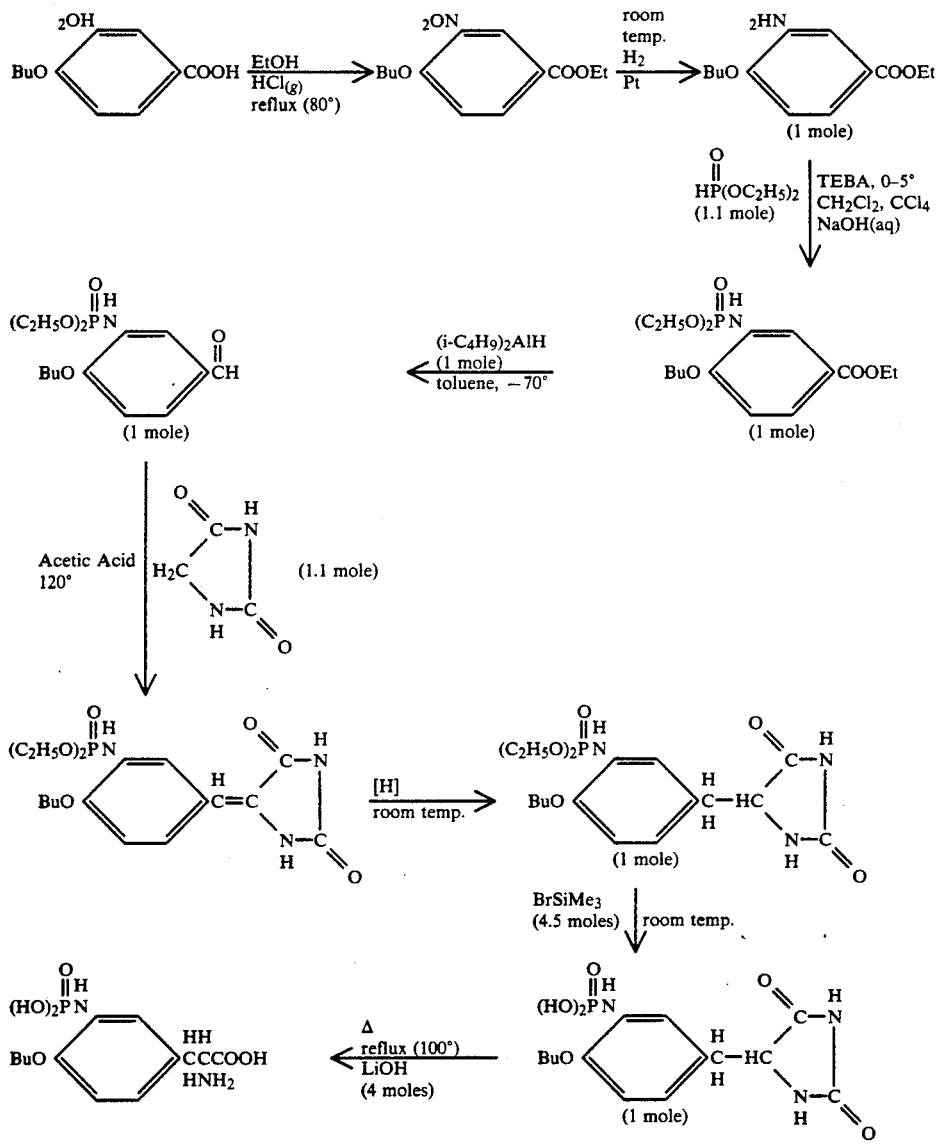

Bu = $CH_3CH_2CH_2CH_2$
Et = $CH_3CH_2$
TEBA = triethylbenzylammonium chloride

EXAMPLE 27

Injectable Composition

A solution was prepared by mixing 500 mg by weight of a phosphorylated derivative of L-dopa as, for example, described in Examples 6, 12, 18 or 24, in the form of its sodium salt, with sufficient sterile water to prepare 2 parts by volume of the final solution. The solution is then placed into 2 ml single dose ampoules.

The above solution is administered to the subject by injection, once a day at a dose rate of 2 ml per day.

EXAMPLE 28

Controlled Release Oral System

Microcapsules of a phosphorylated derivative of L-dopa as, for example, described in Example 6, are prepared by spraying PD granules with a solution of carboxymethylene polymers, (such as "CARBOPOL 934P") to achieve a coating thickness which will gradually release the phsophorylated derivative of L-dopa over an eight hour period.

The above microencapsulated granule are combined in hard gelatin capsules to the extent of 500 mg phosphorylated DOPA derivative per capsule.

The composition is administered to the subject at a daily dose rate of 500 mg (i.e., one capsule per day) for two to four weeks.

EXAMPLE 29

Transdermal Release Composition

An admixture is prepared comprising,

|  | Parts by weight |
| --- | --- |
| Acrylamide copolymer | 20 |
| (e.g., "polytrap FLME 203") | 5 |
| Phosphorylated derivative of L-DOPA, e.g., as described in Example 6 |  |
| Alcohol | 74.9 |
| and a fragrance | 0.1 |

The above mixture is appled to the skin, once a day, preferably in the morning, for two to four weeks.

EXAMPLE 30

Tanning Oil

A. An admixture is prepared by adding in the order indicated:

|  | Parts by weight |
| --- | --- |
| decylolcate | 25.0 |
| isopropyl myristate | 15.0 |
| and propylene glycol dicaprylate/ dicaprate | 5.0 |
| mineral oil | 54.85 |

B. An admixture is prepared by adding 0.01 pbw phosphorylated derivative of L-DOPA, e.g., as described in Examples 6, 12, 18 or 24, to 0.01 pbw of "SOLERTAN PB-10" (a poly(propylene glycol) lanolin ether).

C. The admixture of part B is added to the admixture of part A and the resultant admixture is mixed until homogeneous.

D. The composition of part C is applied to the skin once or twice daily for two to four weeks.

EXAMPLE 31

Suntanning Lotion

An admixture was prepared containing

|  | Parts by weight |
| --- | --- |
| ICI G-1800 | 5.0 |
| (e.g., poly[oxyethylene]21 stearyl ether) |  |
| isopropyl myristate | 10.0 |

-continued

|  | Parts by weight |
| --- | --- |
| preservative | 0.1 |
| stearyl alcohol | 2.0 |
| 2-hydroxy -3,3,5-trimethylhexyl ester of benzoic acid | 8.0 |
| butylated hydroxyanisole | 0.05 |

The above mixture is heated to 70° C. and 60 parts by weight of water, preheated to 70° C. is added thereto. The resultant mixture is stirred and allowed to cool to room temperature.

To the above mixture is then added a 1% citric acid solution, QS, to achieve a pH of 5.0 after which 0.01 parts by weight of a phosphorylated derivative of L-DOPA, for example, as according to Examples 6, 12, 18 or 24, is added, as well as sufficient deionized water to yield 100 parts by weight of lotion.

The above lotion is applied to the skin one-half (½) hour prior to exposure to the sun. After swimming, sweating or towelling, as well as after each hour of exposure, the lotion is reapplied.

EXAMPLE 32

Stimulation of Pigmentation and Tyrosinase Activity in Cultured Melanoma Cells Cloudman S91 mouse melanoma cells were cultured according to the method of John Pawelek, "Methods for Serum-Free Culture of Neuronal and Lymphoid Cells", see p. 61 in *Cell Culture Methods For Molecular and Cell Biology*, Vol. 4, Editors David W. Barnes, David A. Sarbasku and Gordon H. Sato, Pub: Allan R. Liss, N.Y., N.Y.

Cells were grown with or without beta melantropins (MSH)($10^{-8}$M) included in the culture media. Also included in the culture media were p-dopa (described in U.S. Pat. No. 4,508,706, the entire contents of which are incorporated by reference herein) or the four subsets of compounds of the formula

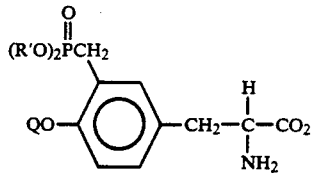

wherein R' is H and Q is either a hydrogen, methoxy, ethoxy, or butoxy group. The compounds were added at concentrations of $10^{-7}$, $10^{-5}$, or $10^{-3}$M.

After four days in culture, with one change of media, the cells were harvested from the culture flasks with EDTA (Pawelek, "Methods for Serum-Free Culture of Neuronal and Lymphoid Cells", supra), pelleted by centrifugation, and the color of the pellets was visually noted by multiple blind observers. The cell number was determined with a Coulter Counter, and the cells were lysed in a non-ionic detergent (Triton X100 vol/vol) at a concentration of $2 \times 10^6$ cell/ml detergent. 75 microliters of cell lysate (representing $1.5 \times 10^5$ lysed cells) were then assayed for tyrosinase activity (see p. 64 in Pawelek, "Methods for Serum-Free Culture of Neuronal and Lymphoid Cells", supra), using formation of tritiated water from tritiated tyrosine as the assay.

Tyrosinase is an enzyme in pigment cells which catalyzes the rate-limiting steps in melanin synthesis. In most cases, and that includes Cloudman melanoma cells in culture, tyrosinase activity is proportional to melanin content of the cells. Thus, measuring tyrosinase is analogous to measuring melanin. The units for measuring tyrosinase are "cpm of tritiated water formed".

In the absence of MSH, pigmentation and tyrosinase activities were extremely low whether or not the various forms of phosphorylated dopa were added to the culture media. The counts per minute of tritiated water formed averaged about 200 in most cases. The hydroxy and ethoxy compounds appeared to stimulate tyrosinase, but nonetheless to a lower extent than when MSH was added to the media. See FIG. 1.

Figure 2:
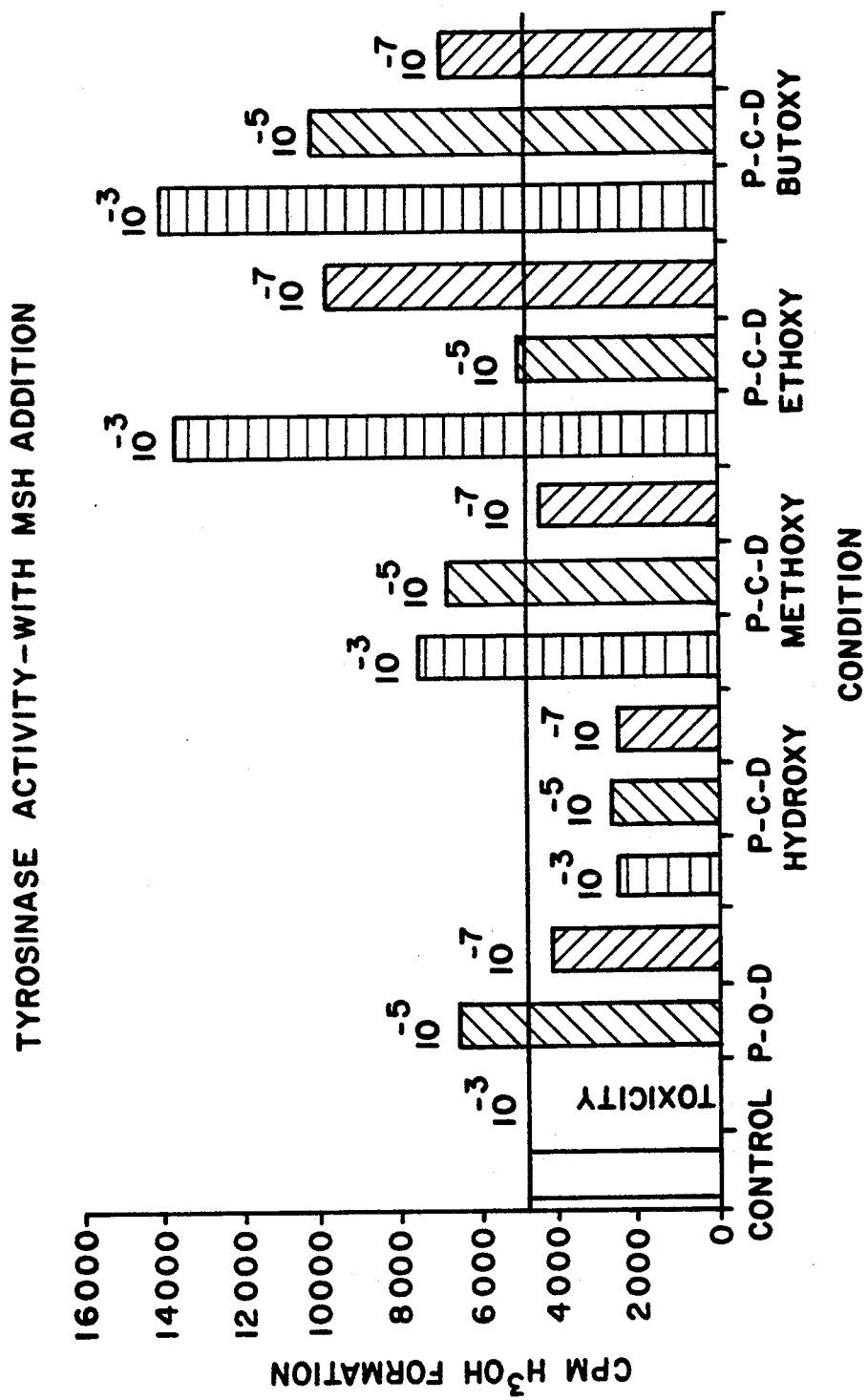
FIG. 2 is a series of bar graphs depicting tryosinase activity in cultured melanoma cells with addition of MSH for p-dopa and for compounds according to the invention.

MSH itself increased the tritiated water formation to about 4400 cpm. Where the various compounds were added, they stimulated tyrosinase activity to different degrees above the MSH stimulation (as much as 2.5 fold in some cases as shown in FIG. 2).

Visually, the melanin present in the cell pellets was proportional to the tyrosinase activity. That is, for example, $10^{-3}$M butoxy and ethoxy compounds along with MSH gave a much stronger pigment response than just MSH alone.

It is noted that MSH is more or less equivalent to UV light, (see Bolognia, Murray and Pawelek, *J. Invest. Dermatology*, (1989)). In culture, MSH is used as the synergistic agent for the phosphodopas, on animals UV light is used.

EXAMPLE 33

Stimulation of Pigmentation in Guinea Pigs with the Butoxy P-C Dopa and Low Levels of UV Light A guinea pig was shaved. An anterior square received ultraviolet B radiation (UVB) only (400 mJ/cm$^2 \times 4$ days) plus vehicle. A posterior square received UVB+20 microliters of a 0.02% solution of the butoxy compound daily for four days and applied manually with latex gloves in a vehicle of tris and glycerol (See Methods section in Bolognia, Murray, and Pawelek, *J. Invest. Dermatology*, (1989)), for vehicle and methods of applying compounds, administering UVB, etc.). The lateral areas received vehicle only (left) or butoxy compound only (right). The only pigment formation occurred in the posterior square. The conclusion is that the butoxy compound and UVB at low levels stimulated pigment formation.

It will be appreciated that the instant specification and claims are set forth by way of illustration and not limitation, and that various modifications and changes may be made without departing from the spirit and scope of the present invention.

What is claimed is:

1. A method for increasing the melanin content in the skin and hair of a mammal, the method comprising administering to said mammal, alone or in admixture with a pharmaceutically acceptable carrier, an effective amount of a phosphorylated compound of L-dopa of the formula

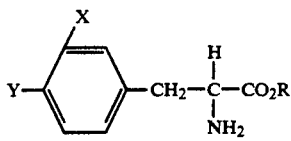

wherein
(a) X is

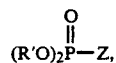

Z is —CH$_2$, N or S, and Y is OQ, wherein Q is H or an alkyl radical with one to twelve carbon atoms, or
(b) X is Q, Y is

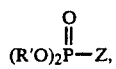

and
R' is hydrogen or a pharmaceutically acceptable cation, and
R is selected from the group consisting of hydrogen, a pharmaceutically acceptable cation, an alkyl radical having one to twelve carbon atoms, an alkenyl radical having two to twelve carbon atoms, an alkinyl radical having two to twelve carbon atoms, phenyl, biphenyl, naphthyl or cycloalkyl having three to eight carbon atoms.

2. A method according to claim 1, wherein the phosphorylated compound of L-dopa is

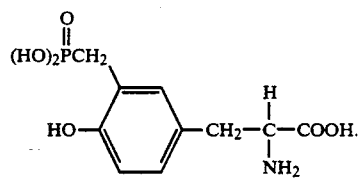

3. A method according to claim 1, wherein the phosphorylated compound of L-dopa is

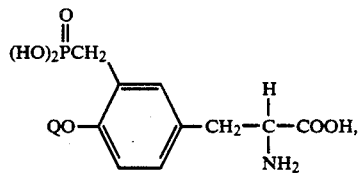

wherein Q is selected from the group consisting of CH$_3$, CH$_3$CH$_2$ and CH$_3$CH$_2$CH$_2$CH$_2$.

4. A method according to claim 3, wherein Q is CH$_3$.

5. A method according to claim 3, wherein Q is CH$_3$CH$_2$.

6. A method according to claim 3, wherein Q is CH$_3$CH$_2$CH$_2$.

7. A method according to claim 1, wherein said mammal is a human being.

8. A method according to claim 7, wherein said human suffers from a disorder of hypopigmentation.

9. A method according to claim 8, wherein the disorder of hypopigmentation is vitiligo.

10. A method according to claim 1, wherein the increased melanization imparts a naturally appearing tan to the skin of a human being.

11. A method according to claim 1, wherein said carrier comprises at least one additive selected from the group consisting of sun screening agents, preservatives, chelating agents, solvents and acidity regulators.

12. A method according to claim 1, further comprising the step of exposing the skin of the mammal to a source of ultra-violet radiation during or after administration of the phosphorylated derivative of L-dopa for a time sufficient to develop melanization in said skin.

13. A method according to claim 1, wherein said carrier is a cosmetic base and the composition is administered topically.

14. A method according to claim 1, wherein the composition is administered transdermally.

15. A method according to claim 1, wherein the carrier is a solvent suitable for parenteral administration and the composition is administered parenterally.

16. A method according to claim 1, wherein the composition is administered orally.

17. A method according to claim 1, wherein R' is a cation selected from the group consisting of sodium, potassium, calcium magnesium, triethanolamine and tris(hydroxymethyl)aminomethane.

* * * * *

UNITED STATES PATENT AND TRADEMARK OFFICE
CERTIFICATE OF CORRECTION

PATENT NO. : 5,100,654

DATED : March 31, 1992

INVENTOR(S) : Pawelek et al.

It is certified that error appears in the above-identified patent and that said Letters Patent is hereby corrected as shown below:

Col. 30, line 9   Delete " Q " and substitute -- OQ --

Signed and Sealed this

Seventh Day of September, 1993

Attest:

BRUCE LEHMAN

*Attesting Officer*    *Commissioner of Patents and Trademarks*